USOO5514544A

United States Patent [19]
Rao et al.

[11] Patent Number: 5,514,544
[45] Date of Patent: May 7, 1996

[54] ACTIVATOR GENE FOR MACROLIDE BIOSYNTHESIS

[75] Inventors: Ramachandra N. Rao, Indianapolis; Jan R. Turner, Carmel, both of Ind.

[73] Assignee: Eli Lilly and Company, Indianapolis, Ind.

[21] Appl. No.: 736,178

[22] Filed: Jul. 26, 1991

[51] Int. Cl.[6] .............................. C12Q 1/68; C07H 21/04
[52] U.S. Cl. ............................ 435/6; 536/23.7; 536/24.1; 935/78
[58] Field of Search .............................. 435/6; 536/23.7, 536/24.1; 935/78

[56] References Cited

U.S. PATENT DOCUMENTS

| 4,935,340 | 6/1990 | Baltz et al. | 435/6 |
| 5,098,837 | 3/1992 | Beckmann et al. | 435/172.3 |

OTHER PUBLICATIONS

Richardson, M. A., et al. (1990) *Journal of Bacteriology* 172(7):3790–2798.
Fernandez–Moreno, M. A., et al. (1991) *Cell* 66:769–780.
Raibaud, A., et al. (1991) *Journal of Bacteriology* 173(14):4454–4463.
Chater, Keith F. (1990) *Biotechnology* 8:115–121.
Chater, Keith F. (1989) *Trends in Genetics* 5(11):372–377.
Hutchinson, C. Richard, et al. (1989) *Journal of Medicinal Chemistry* 32:929–937.
Hopwood, D. A., (1989) *Phil Trans. R. Soc. Lond.* B324:549–562.

*Primary Examiner*—Margaret Parr
*Assistant Examiner*—Kenneth R. Horlick
*Attorney, Agent, or Firm*—Paul J. Gaylo; Robert A. Conrad; John E. Parrish

[57] ABSTRACT

A gene encoding activator protein (srmR) for increasing transcriptional efficiency of macrolide biosynthetic genes is disclosed and claimed. Methods for using srmR to increase macrolide biosynthetic gene transcription and identifying further macrolide biosynthetic pathways are disclosed. Recombinant DNA vectors comprising the srmR gene are disclosed.

3 Claims, 2 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2312 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 345..2312

( x i ) SEQUENCE DESCRIPTION: SEQ ID NO:1:

```
TGCTCGTTCC  GCCGGAAATC  ACGGTGTGGC  CCCCGGGCCA  CCGGGTAGCT  TATGCCTCGT        60

TCACCGCAGC  GGTTGAAGAG  GCAGCCTTCA  ACCCCGGCCC  GGCCTTTATG  GAATTCATTT       120

CCACCGTGCC  GCAACACCCC  TGAAGGACGG  CCGGATATCG  GCCATGAAGC  CCCGGCCTTT       180

CAGCCAGGCG  CCCTCTCTTG  TCGAATAGAG  TATGTCCTCC  GCTGAAGCCG  CCGAAGACGG       240

ACGAAGGGGA  CGAACGGTCA  CCTCGGTCGA  TCTAGACGGA  ATCCTTGAAA  GCGTAATAGC       300

CTGTCAATGC  TTTGGTAAAG  CACAGGGATG  GGGGTGCCTG  CGGG ATG AGT GAC CTG        356
                                                    Met Ser Asp Leu
                                                     1
```

| | | | | | | | | | | | | | | | | |
|---|---|---|---|---|---|---|---|---|---|---|---|---|---|---|---|---|
| GGT | TCT | GGT | GAA | GAA | GGG | TCC | GAA | GAA | GAC | GAG | TCG | GAC | GAC | GCA | CTC | 404 |
| Gly | Ser | Gly | Glu | Glu | Gly | Ser | Glu | Glu | Asp | Glu | Ser | Asp | Asp | Ala | Leu | |
| 5 | | | | | 10 | | | | | 15 | | | | | 20 | |
| GCC | TTC | CTC | GAG | TTC | ATC | GCC | CGG | TCG | GCA | CCA | CGG | AGC | GAA | TAC | GAC | 452 |
| Ala | Phe | Leu | Glu | Phe | Ile | Ala | Arg | Ser | Ala | Pro | Arg | Ser | Glu | Tyr | Asp | |
| | | | | 25 | | | | | 30 | | | | | 35 | | |
| CGG | CTC | ATG | GCC | CGC | GCC | GAA | CGC | TCG | GGC | GCC | GAC | GAG | GAC | CGG | ATG | 500 |
| Arg | Leu | Met | Ala | Arg | Ala | Glu | Arg | Ser | Gly | Ala | Asp | Glu | Asp | Arg | Met | |
| | | | 40 | | | | | 45 | | | | | 50 | | | |
| CGC | CGA | CTG | GAG | CGC | TTC | AAC | CGG | CTC | GCC | CTC | ACC | GCG | CAG | TCG | ATG | 548 |
| Arg | Arg | Leu | Glu | Arg | Phe | Asn | Arg | Leu | Ala | Leu | Thr | Ala | Gln | Ser | Met | |
| | | 55 | | | | | 60 | | | | | 65 | | | | |
| ATC | GAG | TAC | CGC | CGC | GAC | CGG | GAG | GCG | GAG | CTC | GCG | GCC | CTG | GTC | GAC | 596 |
| Ile | Glu | Tyr | Arg | Arg | Asp | Arg | Glu | Ala | Glu | Leu | Ala | Ala | Leu | Val | Asp | |
| | 70 | | | | | 75 | | | | | 80 | | | | | |
| GCC | GCG | CAC | GAG | TTC | GTC | GCC | GCC | CGG | CGG | GGC | AAG | GAC | CTG | CTG | GAG | 644 |
| Ala | Ala | His | Glu | Phe | Val | Ala | Ala | Arg | Arg | Gly | Lys | Asp | Leu | Leu | Glu | |
| 85 | | | | | 90 | | | | | 95 | | | | | 100 | |
| TCC | ATC | GCC | CGC | AGA | GCA | CGG | CTG | CTG | CTG | AAG | CTG | GAC | GTC | TCC | TAC | 692 |
| Ser | Ile | Ala | Arg | Arg | Ala | Arg | Leu | Leu | Leu | Lys | Leu | Asp | Val | Ser | Tyr | |
| | | | | 105 | | | | | 110 | | | | | 115 | | |
| GTC | GGC | CTG | CAC | GAG | GAG | GAC | CGG | CCC | GGC | ACG | GTG | GTG | CTG | AGC | GCC | 740 |
| Val | Gly | Leu | His | Glu | Glu | Asp | Arg | Pro | Gly | Thr | Val | Val | Leu | Ser | Ala | |
| | | | 120 | | | | | 125 | | | | | 130 | | | |
| GAC | GGC | AAC | GCG | GTC | AAG | GTC | GCC | GAG | AGC | TAC | CGG | CTG | CCG | GCC | GAC | 788 |
| Asp | Gly | Asn | Ala | Val | Lys | Val | Ala | Glu | Ser | Tyr | Arg | Leu | Pro | Ala | Asp | |
| | | 135 | | | | | 140 | | | | | 145 | | | | |
| GGC | GGA | CTG | GGC | GCC | ATG | GTG | CGC | ACC | TGC | CGC | GCT | CCC | TTC | TGG | ACC | 836 |
| Gly | Gly | Leu | Gly | Ala | Met | Val | Arg | Thr | Cys | Arg | Ala | Pro | Phe | Trp | Thr | |
| | 150 | | | | | 155 | | | | | 160 | | | | | |
| CCG | GAC | TAC | CTC | GGG | GAC | AAC | AGC | TTC | ACG | CAC | GTC | GAG | GCC | GTC | GAC | 884 |
| Pro | Asp | Tyr | Leu | Gly | Asp | Asn | Ser | Phe | Thr | His | Val | Glu | Ala | Val | Asp | |
| 165 | | | | | 170 | | | | | 175 | | | | | 180 | |
| GAC | ATC | GTC | CGC | GCC | GAA | GGC | CTG | CGC | GCG | GTC | CTG | GCC | GTC | CCG | CTG | 932 |
| Asp | Ile | Val | Arg | Ala | Glu | Gly | Leu | Arg | Ala | Val | Leu | Ala | Val | Pro | Leu | |
| | | | | 185 | | | | | 190 | | | | | 195 | | |
| TGC | GCC | GGG | GGC | GAA | CCG | ATG | GGG | GTC | CTC | TAC | GTC | GCC | GAC | CGT | CAG | 980 |
| Cys | Ala | Gly | Gly | Glu | Pro | Met | Gly | Val | Leu | Tyr | Val | Ala | Asp | Arg | Gln | |
| | | | 200 | | | | | 205 | | | | | 210 | | | |
| GTG | CGG | CAT | CTG | ACC | CCC | AAC | GAG | GTC | ACC | CTG | CTG | TGC | TCG | CTC | GCC | 1028 |
| Val | Arg | His | Leu | Thr | Pro | Asn | Glu | Val | Thr | Leu | Leu | Cys | Ser | Leu | Ala | |
| | | 215 | | | | | 220 | | | | | 225 | | | | |
| GAT | CTG | GCC | GCG | GTG | GCG | ATC | GAG | CGC | AAC | CGG | CTG | GTC | GAG | GAG | CTC | 1076 |
| Asp | Leu | Ala | Ala | Val | Ala | Ile | Glu | Arg | Asn | Arg | Leu | Val | Glu | Glu | Leu | |
| | 230 | | | | | 235 | | | | | 240 | | | | | |
| CAC | GAC | ACC | ATC | GGG | CAA | CTG | CGC | CAG | GAC | ATC | GGC | GAG | GCC | CGC | ACC | 1124 |
| His | Asp | Thr | Ile | Gly | Gln | Leu | Arg | Gln | Asp | Ile | Gly | Glu | Ala | Arg | Thr | |
| 245 | | | | | 250 | | | | | 255 | | | | | 260 | |
| GCC | CTC | GCG | CGC | ACC | CGC | AGG | TCC | GCC | GAC | CTC | CAG | TCG | CAC | CTG | GTC | 1172 |
| Ala | Leu | Ala | Arg | Thr | Arg | Arg | Ser | Ala | Asp | Leu | Gln | Ser | His | Leu | Val | |
| | | | | 265 | | | | | 270 | | | | | 275 | | |
| ACG | CAG | GTG | ATG | GAC | AGG | CGC | GGC | GCC | GAC | TCG | TTA | CTC | GCG | ACG | GCC | 1220 |
| Thr | Gln | Val | Met | Asp | Arg | Arg | Gly | Ala | Asp | Ser | Leu | Leu | Ala | Thr | Ala | |
| | | | 280 | | | | | 285 | | | | | 290 | | | |
| GCC | GAG | GCG | CTC | GGC | GGC | GGA | GCC | GGC | CTG | TGC | AGC | CCG | CTC | GGG | CGC | 1268 |
| Ala | Glu | Ala | Leu | Gly | Gly | Gly | Ala | Gly | Leu | Cys | Ser | Pro | Leu | Gly | Arg | |
| | | 295 | | | | | 300 | | | | | 305 | | | | |
| CCG | CTC | GCC | GAG | TAC | GGG | ACC | CTG | CGC | CCC | GTC | GCC | CCC | ACG | GAA | CTG | 1316 |
| Pro | Leu | Ala | Glu | Tyr | Gly | Thr | Leu | Arg | Pro | Val | Ala | Pro | Thr | Glu | Leu | |
| | 310 | | | | | 315 | | | | | 320 | | | | | |

| | | | | | | | | | | | | | | | | |
|---|---|---|---|---|---|---|---|---|---|---|---|---|---|---|---|---|
| CGC | GCG | GCG | TGC | CGC | CGG | GCC | GCC | GAG | ACC | GGC | CGG | CCC | ACC | TCC | GTG | 1364 |
| Arg 325 | Ala | Ala | Cys | Arg 330 | Arg | Ala | Ala | Glu | Thr 335 | Gly | Arg | Pro | Thr | Ser | Val 340 | |
| GCC | CCG | GGG | GTC | TGG | ACG | GTG | CCC | CTG | CTT | CCC | GGG | GGC | AAC | GCC | GGC | 1412 |
| Ala | Pro | Gly | Val | Trp 345 | Thr | Val | Pro | Leu | Leu 350 | Pro | Gly | Gly | Asn | Ala 355 | Gly | |
| TTC | CTG | CTG | ACC | GAC | CTC | GGT | CCG | GAC | GCG | GAC | CAC | ACC | GCC | GTC | CCC | 1460 |
| Phe | Leu | Leu | Thr 360 | Asp | Leu | Gly | Pro | Asp 365 | Ala | Asp | His | Thr | Ala 370 | Val | Pro | |
| CTG | CTC | CCG | ATG | GTC | GCC | CGC | ACC | CTC | GCG | CTG | CAC | CTG | CGC | GTC | CAG | 1508 |
| Leu | Leu | Pro 375 | Met | Val | Ala | Arg | Thr 380 | Leu | Ala | Leu | His | Leu 385 | Arg | Val | Gln | |
| CAC | GAC | GAC | TCC | CCC | AAG | GCG | CAG | AGC | CAC | CAG | GAG | TTC | TTC | GAC | GAC | 1556 |
| His | Asp | Asp 390 | Ser | Pro | Lys | Ala | Gln 395 | Ser | His | Gln | Glu 400 | Phe | Phe | Asp | Asp | |
| CTG | ATC | GGG | GCG | CCC | CGC | TCA | CCC | ACG | CTC | CTC | AGG | GAA | CGC | GCC | CTG | 1604 |
| Leu 405 | Ile | Gly | Ala | Pro 410 | Arg | Ser | Pro | Thr | Leu 415 | Leu | Arg | Glu | Arg | Ala 420 | Leu | |
| ATG | TTC | TCC | CTC | AGC | TTC | CGC | CGC | CCG | CAC | GTG | GTG | CTG | GTG | GCG | GGC | 1652 |
| Met | Phe | Ser | Leu | Ser 425 | Phe | Arg | Arg | Pro | His 430 | Val | Val | Leu | Val | Ala 435 | Gly | |
| GGA | CCC | CGC | GGG | ACC | TCG | CCG | CGG | CTG | GAC | CGG | TCC | GGC | GCC | GAC | TAC | 1700 |
| Gly | Pro | Arg | Gly 440 | Thr | Ser | Pro | Arg | Leu 445 | Asp | Arg | Ser | Gly | Ala 450 | Asp | Tyr | |
| GCG | AAG | GAG | CTC | GGC | GGG | CTG | TGC | AGC | GTG | CGG | GAC | GGC | GCC | GTC | GTC | 1748 |
| Ala | Lys | Glu 455 | Leu | Gly | Gly | Leu | Cys 460 | Ser | Val | Arg | Asp | Gly 465 | Ala | Val | Val | |
| CTG | CTG | CTG | CCC | GGC | GAC | GAC | CCC | GTC | GCC | GTG | GCG | CAG | ACC | GCC | GCC | 1796 |
| Leu 470 | Leu | Leu | Pro | Gly | Asp 475 | Asp | Pro | Val | Ala | Val 480 | Ala | Gln | Thr | Ala | Ala | |
| CCG | GAG | CTG | ACC | GAC | CGC | GCC | GGG | CAC | CCC | GTC | ACC | GTG | GGG | GTC | GCG | 1844 |
| Pro 485 | Glu | Leu | Thr | Asp | Arg 490 | Ala | Gly | His | Pro | Val 495 | Thr | Val | Gly | Val | Ala 500 | |
| GGC | CCC | GCC | TCG | ACC | GTC | GAC | GGC | ATC | GCC | GAC | GCG | CAC | CGT | GAG | GCC | 1892 |
| Gly | Pro | Ala | Ser 505 | Thr | Val | Asp | Gly | Ile 510 | Ala | Asp | Ala | His | Arg 515 | Glu | Ala | |
| GCG | AAG | TGT | CTG | GAG | ACC | CTC | CGC | GCG | CTC | GGC | GGC | GAC | GGC | GGC | ACC | 1940 |
| Ala | Lys | Cys | Leu 520 | Glu | Thr | Leu | Arg | Ala 525 | Leu | Gly | Gly | Asp | Gly 530 | Gly | Thr | |
| GCG | TGC | GCC | TCC | GAC | CTG | GGT | TTC | CTC | GGC | ATG | CTC | CTC | GCC | GAG | GAG | 1988 |
| Ala | Cys | Ala 535 | Ser | Asp | Leu | Gly | Phe 540 | Leu | Gly | Met | Leu | Leu 545 | Ala | Glu | Glu | |
| AAC | GAC | GTC | CCC | GGT | TAC | ATC | AGG | ACG | ACG | ATC | GGC | CCC | GTG | GTC | GAC | 2036 |
| Asn | Asp 550 | Val | Pro | Gly | Tyr | Ile 555 | Arg | Thr | Thr | Ile | Gly 560 | Pro | Val | Val | Asp | |
| TAC | GAC | ACC | CAC | CGC | TTC | ACG | GAT | CTG | GTT | CCC | ACT | CTG | AGG | GTG | TAC | 2084 |
| Tyr 565 | Asp | Thr | His | Arg | Phe 570 | Thr | Asp | Leu | Val | Pro 575 | Thr | Leu | Arg | Val | Tyr 580 | |
| CTG | GAG | TCG | GGC | AGG | AGC | CCC | ACG | CGT | GCC | GCA | GAG | ACA | CTG | CGC | GTG | 2132 |
| Leu | Glu | Ser | Gly | Arg 585 | Ser | Pro | Thr | Arg | Ala 590 | Ala | Glu | Thr | Leu | Arg 595 | Val | |
| CAC | CCG | AAC | ACC | GTC | TCA | CGG | CGG | CTG | GAG | CGC | ATC | GGC | GTA | CTG | CTG | 2180 |
| His | Pro | Asn | Thr 600 | Val | Ser | Arg | Arg | Leu 605 | Glu | Arg | Ile | Gly | Val 610 | Leu | Leu | |
| GGA | GAG | GAC | TGG | CAG | TCA | CCG | GAG | CGG | GTG | CTG | GAC | ATA | CAA | CTG | GCC | 2228 |
| Gly | Glu | Asp 615 | Trp | Gln | Ser | Pro | Glu 620 | Arg | Val | Leu | Asp | Ile 625 | Gln | Leu | Ala | |
| CTG | CGG | CTC | TAT | CAG | GTG | CGC | TCG | GCG | CTC | TCC | TCG | CAA | CCG | GCG | TCC | 2276 |
| Leu | Arg 630 | Leu | Tyr | Gln | Val | Arg 635 | Ser | Ala | Leu | Ser | Ser 640 | Gln | Pro | Ala | Ser | |

```
GAG  ACC  CGG  GCC  GTG  CTC  GGA  TCG  CTG  CGC  GAG  TGA                                2312
Glu  Thr  Arg  Ala  Val  Leu  Gly  Ser  Leu  Arg  Glu
645                      650                      655
```

(2) INFORMATION FOR SEQ ID NO:2:

(i) SEQUENCE CHARACTERISTICS:
        (A) LENGTH: 655 amino acids
        (B) TYPE: amino acid
        (D) TOPOLOGY: linear (ii) MOLECULE TYPE: protein (xi) SEQUENCE DESCRIPTION: SEQ ID NO:2:

```
Met  Ser  Asp  Leu  Gly  Ser  Gly  Glu  Glu  Gly  Ser  Glu  Glu  Asp  Glu  Ser
 1                    5                   10                        15
Asp  Asp  Ala  Leu  Ala  Phe  Leu  Glu  Phe  Ile  Ala  Arg  Ser  Ala  Pro  Arg
               20                   25                        30
Ser  Glu  Tyr  Asp  Arg  Leu  Met  Ala  Arg  Ala  Glu  Arg  Ser  Gly  Ala  Asp
          35                        40                        45
Glu  Asp  Arg  Met  Arg  Arg  Leu  Glu  Arg  Phe  Asn  Arg  Leu  Ala  Leu  Thr
     50                        55                        60
Ala  Gln  Ser  Met  Ile  Glu  Tyr  Arg  Arg  Asp  Arg  Glu  Ala  Glu  Leu  Ala
65                        70                        75                        80
Ala  Leu  Val  Asp  Ala  Ala  His  Glu  Phe  Val  Ala  Ala  Arg  Arg  Gly  Lys
                    85                        90                        95
Asp  Leu  Leu  Glu  Ser  Ile  Ala  Arg  Arg  Ala  Arg  Leu  Leu  Leu  Lys  Leu
               100                       105                       110
Asp  Val  Ser  Tyr  Val  Gly  Leu  His  Glu  Glu  Asp  Arg  Pro  Gly  Thr  Val
          115                       120                       125
Val  Leu  Ser  Ala  Asp  Gly  Asn  Ala  Val  Lys  Val  Ala  Glu  Ser  Tyr  Arg
     130                       135                       140
Leu  Pro  Ala  Asp  Gly  Gly  Leu  Gly  Ala  Met  Val  Arg  Thr  Cys  Arg  Ala
145                       150                       155                       160
Pro  Phe  Trp  Thr  Pro  Asp  Tyr  Leu  Gly  Asp  Asn  Ser  Phe  Thr  His  Val
                    165                       170                       175
Glu  Ala  Val  Asp  Asp  Ile  Val  Arg  Ala  Glu  Gly  Leu  Arg  Ala  Val  Leu
               180                       185                       190
Ala  Val  Pro  Leu  Cys  Ala  Gly  Gly  Glu  Pro  Met  Gly  Val  Leu  Tyr  Val
          195                       200                       205
Ala  Asp  Arg  Gln  Val  Arg  His  Leu  Thr  Pro  Asn  Glu  Val  Thr  Leu  Leu
     210                       215                       220
Cys  Ser  Leu  Ala  Asp  Leu  Ala  Ala  Val  Ala  Ile  Glu  Arg  Asn  Arg  Leu
225                       230                       235                       240
Val  Glu  Glu  Leu  His  Asp  Thr  Ile  Gly  Gln  Leu  Arg  Gln  Asp  Ile  Gly
                    245                       250                       255
Glu  Ala  Arg  Thr  Ala  Leu  Ala  Arg  Thr  Arg  Arg  Ser  Ala  Asp  Leu  Gln
               260                       265                       270
Ser  His  Leu  Val  Thr  Gln  Val  Met  Asp  Arg  Arg  Gly  Ala  Asp  Ser  Leu
          275                       280                       285
Leu  Ala  Thr  Ala  Ala  Glu  Ala  Leu  Gly  Gly  Gly  Ala  Gly  Leu  Cys  Ser
     290                       295                       300
Pro  Leu  Gly  Arg  Pro  Leu  Ala  Glu  Tyr  Gly  Thr  Leu  Arg  Pro  Val  Ala
305                       310                       315                       320
Pro  Thr  Glu  Leu  Arg  Ala  Ala  Cys  Arg  Arg  Ala  Ala  Glu  Thr  Gly  Arg
                    325                       330                       335
Pro  Thr  Ser  Val  Ala  Pro  Gly  Val  Trp  Thr  Val  Pro  Leu  Leu  Pro  Gly
```

|   |   |   |   |   | 340 |   |   |   |   | 345 |   |   |   |   | 350 |   |   |
|---|---|---|---|---|---|---|---|---|---|---|---|---|---|---|---|---|---|
| Gly | Asn | Ala 355 | Gly | Phe | Leu | Leu | Thr 360 | Asp | Leu | Gly | Pro | Asp 365 | Ala | Asp | His |
| Thr | Ala 370 | Val | Pro | Leu | Leu | Pro 375 | Met | Val | Ala | Arg | Thr 380 | Leu | Ala | Leu | His |
| Leu 385 | Arg | Val | Gln | His | Asp 390 | Asp | Ser | Pro | Lys | Ala 395 | Gln | Ser | His | Gln | Glu 400 |
| Phe | Phe | Asp | Asp | Leu 405 | Ile | Gly | Ala | Pro | Arg 410 | Ser | Pro | Thr | Leu 415 | Leu | Arg |
| Glu | Arg | Ala | Leu 420 | Met | Phe | Ser | Leu | Ser 425 | Phe | Arg | Arg | Pro | His 430 | Val | Val |
| Leu | Val | Ala 435 | Gly | Gly | Pro | Arg | Gly 440 | Thr | Ser | Pro | Arg | Leu 445 | Asp | Arg | Ser |
| Gly | Ala 450 | Asp | Tyr | Ala | Lys | Glu 455 | Leu | Gly | Gly | Leu | Cys 460 | Ser | Val | Arg | Asp |
| Gly 465 | Ala | Val | Val | Leu | Leu 470 | Leu | Pro | Gly | Asp | Asp 475 | Pro | Val | Ala | Val | Ala 480 |
| Gln | Thr | Ala | Ala | Pro 485 | Glu | Leu | Thr | Asp | Arg 490 | Ala | Gly | His | Pro | Val 495 | Thr |
| Val | Gly | Val | Ala 500 | Gly | Pro | Ala | Ser | Thr 505 | Val | Asp | Gly | Ile | Ala 510 | Asp | Ala |
| His | Arg | Glu 515 | Ala | Ala | Lys | Cys | Leu 520 | Glu | Thr | Leu | Arg | Ala 525 | Leu | Gly | Gly |
| Asp | Gly 530 | Gly | Thr | Ala | Cys | Ala 535 | Ser | Asp | Leu | Gly | Phe 540 | Leu | Gly | Met | Leu |
| Leu 545 | Ala | Glu | Glu | Asn | Asp 550 | Val | Pro | Gly | Tyr | Ile 555 | Arg | Thr | Thr | Ile | Gly 560 |
| Pro | Val | Val | Asp | Tyr 565 | Asp | Thr | His | Arg | Phe 570 | Thr | Asp | Leu | Val | Pro 575 | Thr |
| Leu | Arg | Val | Tyr 580 | Leu | Glu | Ser | Gly | Arg 585 | Ser | Pro | Thr | Arg | Ala 590 | Ala | Glu |
| Thr | Leu | Arg 595 | Val | His | Pro | Asn | Thr 600 | Val | Ser | Arg | Arg | Leu 605 | Glu | Arg | Ile |
| Gly | Val 610 | Leu | Leu | Gly | Glu | Asp 615 | Trp | Gln | Ser | Pro | Glu 620 | Arg | Val | Leu | Asp |
| Ile 625 | Gln | Leu | Ala | Leu | Arg 630 | Leu | Tyr | Gln | Val | Arg 635 | Ser | Ala | Leu | Ser | Ser 640 |
| Gln | Pro | Ala | Ser | Glu 645 | Thr | Arg | Ala | Val | Leu 650 | Gly | Ser | Leu | Arg | Glu 655 |   |

ACTIVATOR GENE FOR MACROLIDE BIOSYNTHESIS

BACKGROUND OF THE INVENTION

Macrolide antibiotics are characterized by the presence of a macrocyclic lactone ring, the aglycone (See generally *Macrolide Antibiotics: Chemistry, Biology and Practice* (S. Omura, ed., Academic Press, New York)). Attached to the aglycone are one or more deoxy sugars. The sugars may be acylated. The macrocyclic ring is commonly 12-, 14-, or 16-membered bum larger rings are also known. The mechanism of action of macrolide antibiotics involves the inhibition of protein synthesis.

The macrolide antibiotics are highly active against gram-positive organisms such as Staphylococcus, Streptococcus, and Diplococcus and also have activity against gram-negative organisms such as *Neisseria Gonorrhea* and *meningitidis, Bordetella pertussis*, and *Haemophilus influenzae*. Id. at p.26. All of the above strains are capable of causing significant illnesses. Macrolides, including spiramycin and tylosin, have been used clinically in the medical and veterinary fields due to their low toxicity. Id. at p.27.

Members of the macrolide family of compounds which are also referred to as macrocyclic lactones have utilities beyond antibiotic activity. For example FK506 has potent immunosuppressive activity and thus offers promise in therapeutic applications such as suppression of organ transplant rejection, rheumatoid arthritis, and various other autoimmune states. Other macrolides such as avermectin have activities including insecticidal and anti-helminthic activities.

Because the macrolides are so clinically useful, it is of the utmost importance to clone the genes responsible for producing the enzymes of the respective biosynthetic pathways. These genes can be used to increase the enzyme concentration in an organism, thereby increasing the efficiency of antibiotic production (Chater, 1990, *Biotechnology* 8: 115–121. The genes may be shuttled among various antibiotic producers to generate hybrid antibiotics, due to the "loose" substrate specificities of some of the biosynthetic enzymes (Sadakane et al., 1982, *J. Anti-biotics* 35:680–687; Hopwood 1989 *Phil. Trans-R. Soc Lond.* B 324: 549–562; Hutchison et al, 1989, Drug Discovery and Development Through The Energetic Engineering of Antibiotic—Producing Microorgansims, *J. Med. Chem.* 32: 929–937). In addition, the cloned genes can serve as substrates for mutagenesis which can lead to alterations in substrate specificity. The genes can also be used to generate strains containing mutant genes by the method of the present invention.

A significant limitation in achieving the above stated goal of cloning antibiotic synthetic pathways is the difficulty in identifying organisms having such pathways. Historically, discovery of antibiotics occurred through evaluation of fermentation broths for anti-bacterial or anti-fungal activity. Such an approach is inadequate in that the biosynthetic pathway would only be implicated by the logical dependence of the product on an underlying biosynthetic pathway leading to its production. U.S. Pat. No. 4,935,340 teaches the use of antibiotic resistance genes as probes for locating macrolide biosynthetic pathways. However the numerous mechanisms whereby resistance to antibiotics is attained and the non-antibiotic utilities of macrolides such as FK506 and avermectin suggests that numerous macrolide biosynthetic pathways could escape detection by the method of U.S. Pat. No. 4,935,340.

SUMMARY OF THE INVENTION

The present invention provides a regulatory (activator) gene, srmR, of the macrolide biosynthetic pathway. SrmR increases transcriptional efficiency of genes within macrolide biosynthetic pathways. Recombinant DNA vectors comprising srmR are thus useful in increasing production levels of macrolides. SrmR is also useful in hybridization studies to detect further macrolide biosynthetic pathways. The present invention provides the srmR gene driven by its promoter. The translation product of the srmR gene is also useful for generation of antibodies which are useful in the detection of other macrolide biosynthetic pathways.

DETAILED DESCRIPTION

The present invention embraces the discovery that the srmR gene of the macrolide biosynthetic pathway of *Streptomyces ambofaciens* functions as a positive regulator (activator) of the macrolide biosynthetic pathway of *Streptomyces ambofaciens* (NRRL 15263).

Cosmid pKC644 comprises an ~32 kb segment of the *Streotomyces ambofaciens* genome. Cosmid pKC644 is publicly available from the Northern Regional Research Laboratory, Peoria, Ill. (NRRL) under the accession number NRRL B-18238. The SrmR gene of the present invention resides within the ~32 kb insert of cosmid eKC644 and thus cosmid pKC644 provides a convenient source of the srmR gene of the present invention.

Figure 1:
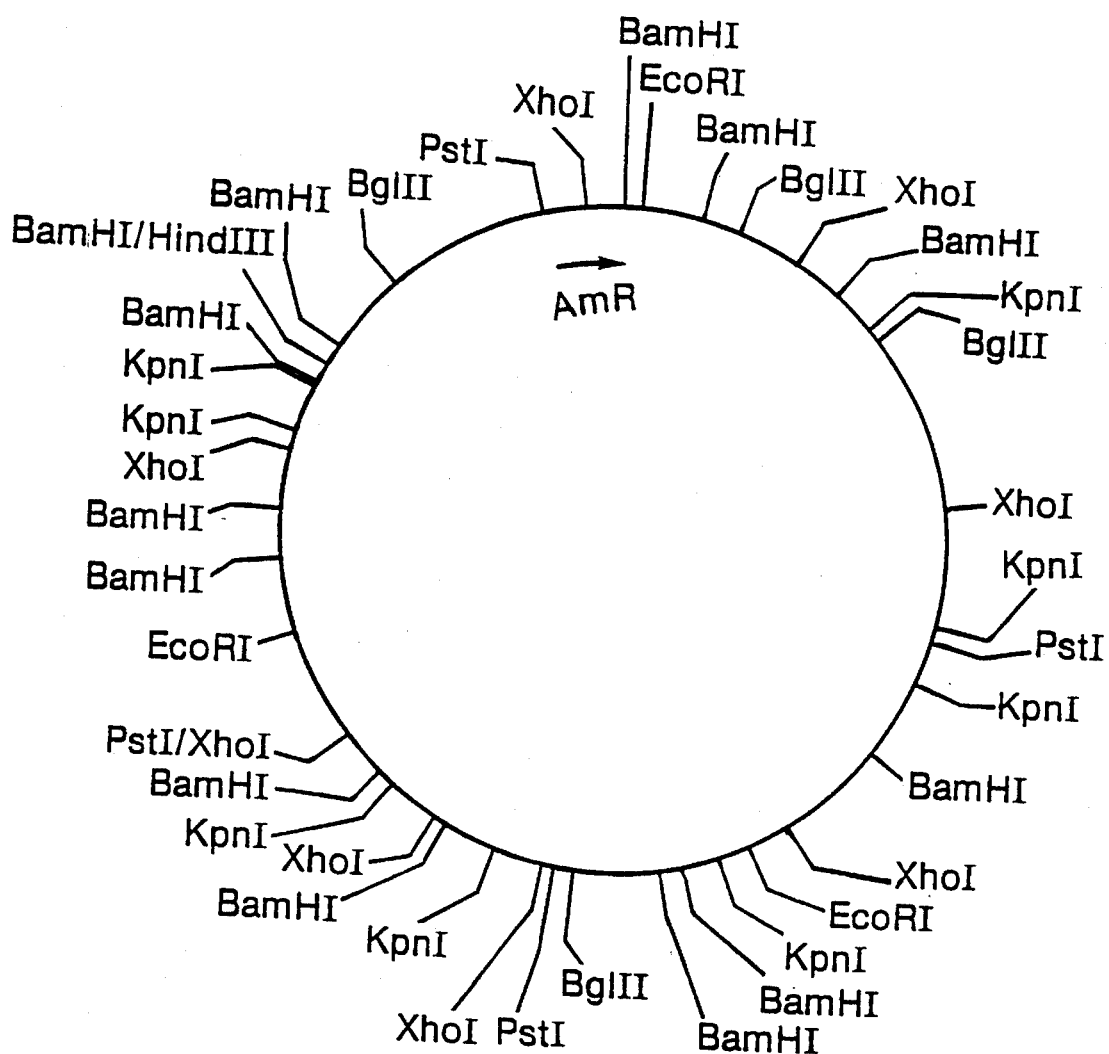
FIG. 1 is a restriction site and function map of Cosmid pKC644.

Cosmid pKC644 is disclosed and claimed in U.S. patent application Ser. No. 07/203,387, filed Jun. 7, 1988, now issued as U.S. Pat. No. 5,098,837, issued Mar. 24, 1992. For convenience, a restriction endonuclease map of cosmid pKC644 is provided in FIG. 1. The organization of macrolide biosynthetic genes within the pKC644 insert derived from the *Streptomyces ambofaciens* genome is delineated in FIG. 2. As evident in FIG. 2, the srmR gene is flanked by numerous restriction endonuclease recognition sequences.

The nucleotide sequence of the srmR gene including its promoter (transcriptional activating sequence) is set forth below in Sequence ID1.

Sequence ID1
```
TGCTCGTTCC GCCGGAAATC ACGGTGTGGC CCCCGGGCCA CCGGGTAGCT

TATGCCTCGT TCACCGCAGC GGTTGAAGAG GCAGCCTTCA ACCCCGGCCC

GGCCTTTATG GAATTCATTT CCACCGTGCC GCAACACCCC TGAAGGACGG

CCGGATATCG GCCATGAAGC CCCGGCCTTT CAGCCAGGCG CCCTCTCTTG
```

-continued

TCGAATAGAG TATGTCCTCC GCTGAAGCCG CCGAAGACGG ACGAAGGGGA

CGAACGGTCA CCTCGGTCGA TCTAGACGGA ATCCTTGAAA GCGTAATAGC

CTGTCAATGC TTTGGTAAAG CACAGGGATG GGGGTGCCTG CGGG ATG AGT

GAC CTG GGT TCT GGT GAA GAA GGG TCC GAA GAA GAC GAG TCG GAC

GAC GCA CTC GCC TTC CTC GAG TTC ATC GCC CGG TCG GCA CCA CGG

AGC GAA TAC GAC CGG CTC ATG GCC CGC GCC GAA CGC TCG GGC

GCC GAC GAG GAC CGG ATG CGC CGA CTG GAG CGC TTC AAC CGG

CTC GCC CTC ACC GCG CAG TCG ATG ATC GAG TAC CGC CGC GAC CGG

GAG GCG GAG CTC GCG GCC CTG GTC GAC GCC GCG CAC GAG TTC GTC

GCC GCC CGG CGG GGC AAG GAC CTG CTG GAG TCC ATC GCC CGC AGA

GCA CGG CTG CTG CTG AAG CTG GAC GTC TCC TAC GTC GGC CTG CAC

GAG GAG GAC CGG CCC GGC ACG GTG GTG CTG AGC GCCGAC GGC AAC

GCG GTC AAG GTC GCC GAG AGC TAC CGG CTG CCG GCC GAC GGC GGA

CTG GGC GCC ATG GTG CGC ACC TGC CGC GCT CCC TTC TGG ACC CCG

GAC TAC CTC GGG GAC AAC AGC TTC ACG CAC GTC GAG GCC GTC GAC

GAC ATC GTC CGC GCC GAA GGC CTG CGC GCG GTC CTG GCC GTC CCG

CTG TGC GCC GGG GGC GAA CCG ATG GGG GTC CTC TAC GTC GCC GAC

CGT CAG GTG CGG CAT CTG ACC CCC AAC GAG GTC ACC CTG CTG TGC

TCG CTC GCC GAT CTG GCC GCG GTG GCG ATC GAG CGC AAC CGG CTG

GTC GAG GAG CTC CAC GAC ACC ATC GGG CAA CTG CGC CAG GAC ATC

GGC GAG GCC CGC ACC GCC CTC GCG CGC ACC CGC AGG TCC GCC GAC

CTC CAG TCG CAC CTG GTC ACG CAG GTG ATG GAC AGG CGC GGC GCC

GAC TCG TTA CTC GCG ACG GCC GCC GAG GCG CTC GGC GGC GGA GCC

GGC CTG TGC AGC CCG CTC GGG CGC CCG CTC GCC GAG TAC GGG ACC

CTG CGC CCC GTC GCC CCC ACG GAA CTG CGC GCG GCG TGC CGC CGG

GCC GCC GAG ACC GGC CGG CCC ACC TCC GTG GCC CCG GGG GTC TGG

ACG GTG CCC CTG CTT CCC GGG GGC AAC GCC GGC TTC CTG CTG ACC

GAC CTC GGT CCG GAC GCG GAC CAC ACC GCC GTC CCC CTG CTC CCG

ATG GTC GCC CGC ACC CTC GCG CTG CAC CTG CGC GTC CAG CAC GAC

GAC TCC CCC AAG GCG CAG AGC CAC CAG GAG TTC TTC GAC GAC CTG

ATC GGG GCG CCC CGC TCA CCC ACG CTC CTC AGG GAA CGC GCC CTG

ATG TTC TCC CTC AGC TTC CGC CGC CCG CAC GTG GTG CTG GTG GCG

GGC GGA CCC CGC GGG ACC TCG CCG CGG CTG GAC CGG TCC GGC GCC

GAC TAC GCG AAG GAG CTC GGC GGG CTG TGC AGC GTG CGG GAC GGC

GCC GTC GTC CTG CTG CTG CCC GGC GAC GAC CCC GTC GCC GTG GCG

CAG ACC GCC GCC CCG GAG CTG ACC GAC CGC GCC GGG CAC CCC GTC

ACC GTG GGG GTC GCG GGC CCC GCC TCG ACC GTC GAC GGC ATC GCC

GAC GCG CAC CGT GAG GCC GCG AAG TGT CTG GAG ACC CTC GCG CG

CTC GGC GGC GAC GGC GGC ACC GCG TGC GCC TCC GAC CTG GGT TTC

CTC GGC ATG CTC CTC GCC GAG GAG AAC GAC GTC CCC GGT TAC ATC

```
AGG ACG ACG ATC GGC CCC GTG GTC GAC TAC GAC ACC CAC CGC TTC

ACG GAT CTG GTT CCC ACT CTG AGG GTG TAC CTG GAG TCG GGC AGG

AGC CCC ACG CGT GCC GCA GAG ACA CTG CGC GTG CAC CCG AAC ACC

GTC TCA CGG CGG CTG GAG CGC ATC GGC GTA CTG CTG GGA GAG GAC

TGG CAG TCA CCG GAG CGG GTG CTG GAC ATA CAA CTG GCC CTG CGG

CTC TAT CAG GTG CGC TCG GCG CTC TCC TCG CAA CCG GCG TCC GAG

ACC CGG GCC GTG CTC GGA TCG CTG CGC GAG TGA
```

The sequence of Sequence ID1 indicates the −35 and −10 sequences, where RNA polymerase can bind to initiate transcription, by underlining. Also evident in Sequence ID1 are three potential translation initiation codons, which are set forth in bold type.

Complementation experiments utilizing the srmR gene of plasmid pKC644 established the ability of srmR to restore macrolide biosynthetic gene transcription in mutants having defective srmR genes due to insertional inactivation of that region of the *S. ambofaciens* genome. See Richardson et al. (1990) *J. Bacteriol*, 172: 3790—3798. Experiments utilizing integrating vectors established the ability of srmR to complement such mutants, while decreasing the possibility of homologous recombination, thereby establishing the ability of srmR to function in trans.

Figure 2:
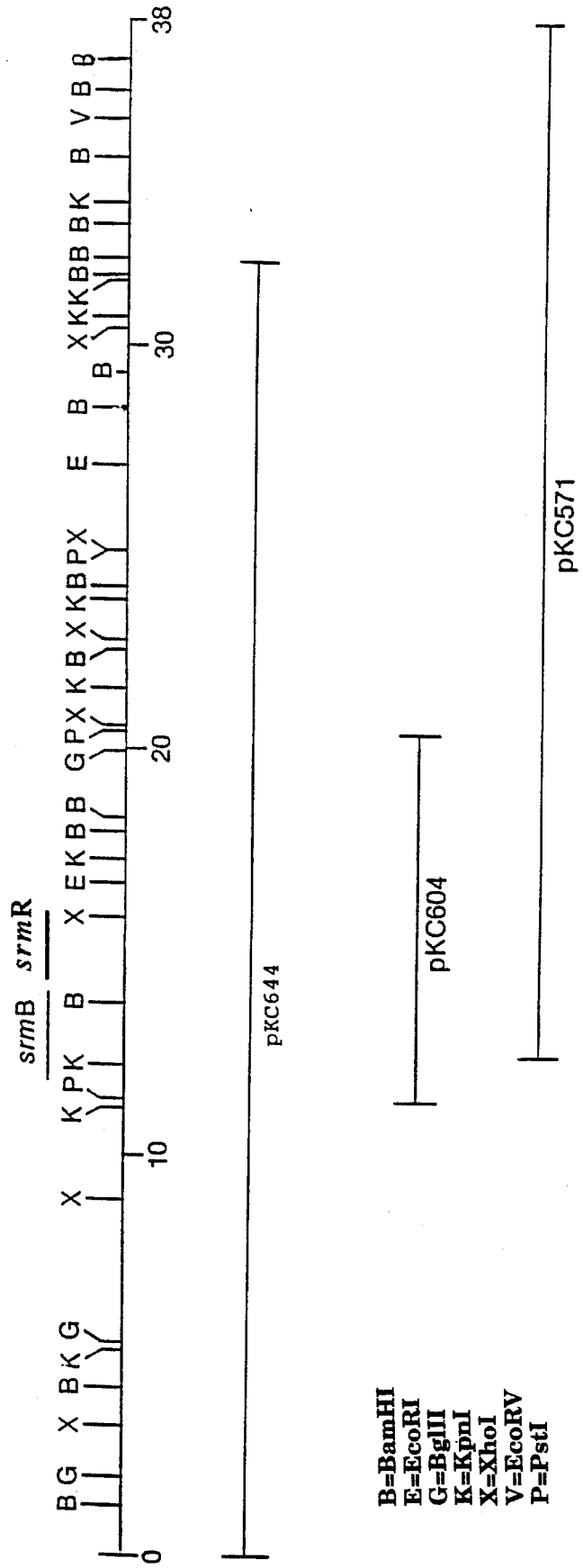
FIG. 2 is a restriction map of Spiramycin Biosynthetic Gene Region of *Streptomyces ambofaciens*.

The ability of the srmR gene product to activate (increase the levels of) macrolide biosynthetic gene transcription affords a novel means for increasing the efficiency of macrolide biosynthesis. Several recombinant DNA vectors comprising the srmR gene have been constructed. The vectors and the region of the *S. ambofaciens* genome they comprise is illustrated in FIG. 2. The construction of such vectors comprising srmR is described in U.S. application Ser. No. 07/203,387, now U.S. Pat. No. 5,098,837 the contents of which are herein incorporated by reference, as well as Richardson, et al., supra. Skilled artisans will appreciate the versatility of approaches to increasing macrolide biosynthesis through exploitation of the srmR gene as embodied in the various autonomously replicating and integrative vectors taught in U.S. application Ser. No. 07/203,387, now U.S. Pat. No. 5,098,837 and otherwise within the skill of the molecular biologists. Other vectors useful in srmR activation of macrolide biosynthetic pathways include derivatives of vectors well known in the art as useful for genetic engineering of Stretomyces. Such vectors include but are not limited to the vectors set forth in Table 1 below.

TABLE I

Streptomyces Plasmids

| Plasmid | Host | Accession Number |
|---|---|---|
| SCP2 | *Streptomyces coelicolor* A3(2) | NRRL 15042 |
| SCP2* | *Streptomyces coelicolor* M110 | NRRL 15041 |
| pEL7 | *Streptomyces ambofaciens*/pEL7 | NRRL 12523 |
| pUC6 | *Streptomyces espinosus* | NRRL 11439 |
| pUC3 | Streptomyces 3022A | NRRL 11441 |
| SLP1 | *Streptomyces lividans* | NCIB[1] 11417 |
| pNM100 | *Streptomyces virginiae* | NRRL 15156 |
| pEL103 | *Streptomyces granuloruber* A399 12.13/pEL103 | NRRL 12549 |
| pIJ702 | *Streptomyces lividans* | ATCC[2] 39155 |

TABLE I-continued

Streptomyces Plasmids

| Plasmid | Host | Accession Number |
|---|---|---|

[1]National Collection of Industrial Bacteria (NCIB), Torry Research Station, Post Office Box 31, 135 Abbey Road, Aberdeen AB98DG, Scotland, United Kigdom.
[2]American Type Culture Collection, Rockville, MD 20852

Thus, the present invention provides a method for improving the transcriptional efficiency of macrolide biosynthetic genes comprising transforming a macrolide producing streptomycete responsive to such improvement with a recombinant DNA vector comprising the srmR gene operably linked to a transcriptonal activating sequence which is functional in said Streptomycete. The term "transformation" as used in the present invention means introduction of DNA into a host cell by any method including but not limited to: transduction, transformation, conjugation, and electroporation. Determination of an organisms responsiveness to srmR enhancement of macrolide production involves mere routine experimentation.

Macrolide producing organisms suitable for use with the srmR activation aspect of the present invention include organisms such as those set forth in Table II below.

TABLE II

Macrolide-Producing Organisms

| Organism | Product |
|---|---|
| *Micromonospora rosarla* | rosaramicin |
| *Streptomyces* | |
| albireticuli | carbomycin |
| albogriseolus | mikonomycin |
| albus | albomycetin |
| albus var. coilmyceticus | coleimycin |
| ambofaciens | spiramycin and foromacidin D |
| antibioticus | oleandomycin |
| avermitills | avermectins |
| bikiniensis | chalcomycin |
| bruneogriseus | albocycline |
| caelestis | M188 and celesticetin |
| cinerochromogenes | cineromycin B |
| cirratus | cirramycin |
| deltae | deltamycins |
| djakartensis | niddamycin |
| erythreus | erythromycins |
| eurocidicus | methymycin |
| eurYthermus | angolamycin |
| fasciculus | amaromycin |
| felleus | argomycin and |

TABLE II-continued

Macrolide-Producing Organisms

| Organism | Product |
|---|---|
| | picromycin |
| fimbriatus | amaromycin |
| flavochromogenes | amaromycin and shincomycins |
| fradiae | tylosin |
| fungicidicus | NA-181 |
| fungicidicus var. espinomyceticus | espinomycins |
| furdicidicus | mydecamycin |
| goshikiensis | bandamycin |
| griseofaciens | PA133A and B |
| griseoflavus | acumycin |
| griseofuscus | bundlin |
| griseolus | griseomycin |
| griseospiralis | relomycin |
| griseus | borrelidin |
| Streptomyces griseus. ssp. sulphurus | bafilomycins |
| halstedi | carbomycin and leucanicid: |
| hygroscopicus | tylosin |
| hygroscopicus subsp. aureolacrimosus | milbemycins |
| kitastoensis | leucomycin A₃ and josamycin |
| lavendulae | aldgamycin |
| loidensis | vernamycin A and B |
| macrosporeus | carbomycin |
| maizeus | lngramycin |
| mycarofaciens | acetyl-leukomycin, and esplnomycln |
| narbonensis | josamycin and narbomycin |
| narbonensis var. iosamyceticus | leucomycin A₃ and josamycin |
| olivochromogenes | oleandomycin |
| platensis | platenomycin |
| rimosus | tylosin and neutramycin |
| rochei | lankacidin and borrelidin |
| roseochromogenes | albocycline |
| roseocitreus | albocycline |
| spinichromogenes var. suragaoensis | kujimycins |
| tendae | carbomycin |
| thermotolerans | carbomycin |
| venezuelae | methymycins |
| violaceoniger | lankacidins and lankamycin |

The srmR gene is also useful to construct probes for the facile screening of organisms for the presence of macrolide biosynthetic pathways having activator sequences. It is well known in the art that many biosynthetic pathways are clustered. Chater, 1990, *Biotechnology* 8: 115–121; Sadakane et al., 1982, *J. Antibiotics* 35:680–687; Hopwood, 1989, *Phil. Trans-R. Soc. Lond. B* 324: 549–562; and Hutchison et al., 1989, Drug Discovery and Development Through The Energetic Engineering of Antibiotic—Producing Microorgansims, *J. Med. Chem.* 32: 929–937.

The sequence of srmR. provided by the present invention allows skilled artisans to construct probes corresponding to the coding region of the crmR gene. Such probes can be "labeled" to allow detection of the probes upon binding to a DNA sequence having homology with the probe. Methods for labelling probes with $^{32}p$ or biotin are well known in the art. U.S. Pat. No. 4,935,340, which is herein incorprated by reference, teaches labelling techniques and hybridization protocols. Oligonucleotide synthesis and labelling as well as hybridization protocols are also detailed in Sambrook et al., *Molecular Cloning* (1982) and Ausubel, et al., *Current Protocols in Molecular Biology*, (1988). Thus, the srmR gene sequence in combination with labelling and hybridization techniques, which are well known in the art, allow the facile detection of macrolide biosynthetic pathways having activator genes which hybridize with srmR probes. Skilled artisans realize that panels of probes representing various regions of the srmR coding sequence should be used to optimize the detection of such macrolide biosynthetic pathways.

Organisms which would be of interest for purposes of determining the presence of macrolide biosynthetic pathways are limited to the actinomycetes. The American Type Culture Collection lists numerous such organisms while numerous other are available from culture depositories such as the NRRL. Procedures for isolating actinomycetes from soil samples are well known. See Hopwood, et al, *Genetic Manipulation of Streptomyces, A Laboratory Manual* (1985). The phrase "DNA samples of interest" is defined for purposes of the present invention as DNA prepared from an actinomycete, whether in a genomic library or as a total DNA preparation from a culture of an actinomycete. Preparation of such genomic libraries is well known in the arm (See U.S. Pat. No. 4,935,340, *Molecular Cloning*, supra., *Current Protocols in Molecular Biology*, supra and *Genetic Manipulation of Streptomyces. A Laboratory Manual*, supra.).

The amino acid sequence of the potential srmR translation product is presented in Sequence ID2.

Sequence ID2

Met Ser Asp Leu Gly Ser Gly Glu Glu Gly Ser Glu Glu Asp Glu

Ser Asp Asp Ala Leu Ala Phe Leu Glu Phe Ile Ala Arg Ser Ala

Pro Arg Ser Glu Tyr Asp Arg Leu Met Ala Arg Ala Glu Arg Ser

Gly Ala Asp Glu Asp Arg Met Arg Arg Leu Glu Arg Phe Asn Arg

Leu Ala Leu Thr Ala Gln Ser Met Ile Glu Tyr Arg Arg Asp Arg

Glu Ala Glu Leu Ala Ala Leu Val Asp Ala Ala His Glu Phe Val

Ala Ala Arg Arg Gly Lys Asp Leu Leu Glu Ser Ile Ala Arg Arg

Ala Arg Leu Leu Leu Lys Leu Asp Val Ser Tyr Val Gly Leu His

Glu Glu Asp Arg Pro Gly Thr Val Val Leu Ser Ala Asp Gly Asn

Ala Val Lys Val Ala Glu Ser Tyr Arg Leu Pro Ala Asp Gly Gly

Leu Gly Ala Met Val Arg Thr Cys Arg Ala Pro Phe Trp Thr Pro

Asp Tyr Leu Gly Asp Asn Ser Phe Thr His Val Glu Ala Val Asp

Asp Ile Val Arg Ala Glu Gly Leu Arg Ala Val Leu Ala Val Pro

Leu Cys Ala Gly Gly Glu Pro Met Gly Val Leu Tyr Val Ala Asp

Arg Gln Val Arg His Leu Thr Pro Asn Glu Val Thr Leu Leu Cys

Ser Leu Ala Asp Leu Ala Ala Val Ala Ile Glu Arg Asn Arg Leu

Val Glu Glu Leu His Asp Thr Ile Gly Gln Leu Arg Gln Asp Ile

Gly Glu Ala Arg Thr Ala Leu Ala Arg Thr Arg Arg Ser Ala Asp

Leu Gln Ser His Leu Val Thr Gln Val Met Asp Arg Arg Gly Ala

Asp Ser Leu Leu Ala Thr Ala Ala Glu Ala Leu Gly Gly Gly Ala

Gly Leu Cys Ser Pro Leu Gly Arg Pro Leu Ala Glu Tyr Gly Thr

Leu Arg Pro Val Ala Pro Thr Glu Leu Arg Ala Ala Cys Arg Arg

Ala Ala Glu Thr Gly Arg Pro Thr Ser Val Ala Pro Gly Val Trp

-continued

Thr Val Pro Leu Leu Pro Gly Gly Asn Ala Gly Phe Leu Leu Thr

Asp Leu Gly Pro Asp Ala Asp His Thr Ala Val Pro Leu Leu Pro

Met Val Ala Arg Thr Leu Ala Leu His Leu Arg Val Gln His Asp

Asp Ser Pro Lys Ala Gln Ser His Gln Glu Phe Phe Asp Asp Leu

Ile Gly Ala Pro Arg Ser Pro Thr Leu Leu Arg Glu Arg Ala Leu

Met Phe Ser Leu Ser Phe Arg Arg Pro His Val Val Leu Val Ala

Gly Gly Pro Arg Gly Thr Ser Pro Arg Leu Asp Arg Ser Gly Ala

Asp Tyr Ala Lys Glu Leu Gly Gly Leu Cys Ser Val Arg Asp Gly

Ala Val Val Leu Leu Leu Pro Gly Asp Asp Pro Val Ala Val Ala

Gln Thr Ala Ala Pro Glu Leu Thr Asp Arg Ala Gly His Pro Val

Thr Val Gly Val Ala Gly Pro Ala Ser Thr Val Asp Gly Ile Ala

Asp Ala His Arg Glu Ala Ala Lys Cys Leu Glu Thr Leu Arg Ala

Leu Gly Gly Asp Gly Gly Thr Ala Cys Ala Ser Asp Leu Gly Phe

Leu Gly Met Leu Leu Ala Glu Glu Asn Asp Val Pro Gly Tyr Ile

Arg Thr Thr Ile Gly Pro Val Val Asp Tyr Asp Thr His Arg Phe

Thr Asp Leu Val Pro Thr Leu Arg Val Tyr Leu Glu Ser Gly Arg

Ser Pro Thr Arg Ala Ala Glu Thr Leu Arg Val His Pro Asn Thr

Val Ser Arg Arg Leu Glu Arg Ile Gly Val Leu Leu Gly Glu Asp

Trp Gln Ser Pro Glu Arg Val Leu Asp Ile Gln Leu Ala Leu Arg

Leu Tyr Gln Val Arg Ser Ala Leu Ser Ser Gln Pro Ala Ser Glu

Thr Arg Ala Val Leu Gly Ser Leu Arg Glu

Sequence ID2 presents the amino acid sequence of the translation product of the srmR gene assuming the translation initiates at the first ATG (potential translation initiation codon) of Sequence ID1. Skilled artisans realize that the actual SrmR translation product may be shorter depending upon which ATG codon serves as the translation initiation codon or alternatively that 3 forms of the srmR activator protein may occur, each originating at one of the potential translation initiation codons. Determination of the translation initiation codon is well within the skill off the art and requires only that the srmR protein be isolated and subjected to N terminal sequence analysis.

The translation products of the srmR gene are useful in preparing antibodies which can be used to screen organisms for the presence of activator proteins such as srmR, the presence of which is indicative of macrolide biosynthetic capacity. The srmR translation product can be isolated using standard purification methods for use as an immunogen either from Streptomyces species transformed with srmR expression vectors such as pKC644. Alternatively and preferably amino acid sequences are selected from the known amino acid sequence of srmR and synthesized by solid phase amino acid synthesis for use in routine immunization protocols. Solid phase amino acid synthesis is well known in the art. Immunization protocols suitable for producing srmR reactive antiserums are taught in numerous Immunological Methods books such as Mishell, et al., Selected Methods in Cellular Immunology (1980) and Langone, et al., *Methods in Enzymology*, Volume 73, (1981). SrmR reactive antibodies can be purified using well known reagents such as Cyanogen Bromide Activated Sepharose (Pharmacia Fine Ckemicals) as matrices for coupling the amino acid sequences utilized as immunogens which in turn can be utilized as affinity chromatography resins for purifying srmR reactive antibodies. The general methodology for constructing and utilizing affinity matrices is detailed in Pharmacia's product literature entitled "Affinity Chromatography—Principles and Methods" which is available upon request from Pharmacia as well as *Methods in Enzymology*, Volume 73, supra.

Monoclonal antibody production is likewise well known in the art of immunology. See Methods in Enzymology, Volume 73, supra.

The srmR reactive antibodies are useful for detecting activator proteins such as srmR in a variety of routine immunochemical analysis such as enzyme linked immunosorbent assays, radioimmunoassay, and the like. See Methods in Enzymology, Volume 73, supra. Organisms being subjected to such immunoassays can be lysed and dried to the bottoms of 96 well microfilter plates as described by Starling, J. J., et al., (1982) *Cancer Research* 42; 3084 et seq. followed by contacting the sample of interest (the dried cell lysates) with a srmR reactive antibody which can either be directly labelled with a detector group such as $^{125}$I, alkaline phosphatase, horse-radish peroxidase, avidin or alternatively, the anti-srmR antibody, can be detected by addition of a secondary reagent which specifically binds or the srmR reactive antibody and which is labelled with a detector group. *Methods in Enzymology*, Volume 73, supra details a variety of approaches to immunoassays, any one of which could readily be used for purposes of the present invention and which would require mere routine experimentation to perfect.

EXAMPLE 1

Isolation of Cosmid pKC644

Cosmid pKC644 (FIG. 1) can be obtained from the Northern Regional Research Center (NRRL), Peoria, Ill. 61604, in *E. coli* K12 DK22 under the accession number NRRL B-18238. The pKC644 cosmid DNA was used to isolate genes of the present invention and to generate spiramycin biosynthetic mutant strains. The lyophils of *E. coli* K12 DK22/pKC644 were plated onto L-agar plates (10 g of trypone, 10 g of NaCl, 5 g of yeast extract, and 15 g of agar per liter) containing 200 μg/ml apramycin to obtain a single colony isolate of the strain. This colony was used to inoculate about 500 ml of L broth (L agar without agar) containing 200 μg/ml apramycin, and the resulting culture was incubated at 30° C. with aeration until the cells reached stationary phase.

Cosmid DNA was obtained from the cells in accordance with the procedure of Rao et al., 1987 in *Methods in Enzymology*, 153:166–198 (R. Wu and L. Grossman, eds., Academic Press, New York), described below.

The cells were centrifuged at 8000 rpm for 10 minutes. After the supernatant was decanted, the cells were resuspended in 7 ml of 25% sucrose, 50 mM Tris HCl, pH 8.0. Freshly prepared lysozyme (0.25 ml of a 5 mg/ml solution) was added to the solution, along with 0.4 ml of 0.5M EDTA (pH 8), and 0.05 ml of 5 mg/ml RNase A. The mixture was incubated for 15 minutes at 37° C. To this 0.75 ml of Triton lyric mix (150 mM Tris HCl, pH 8.0, 3% Triton X-100 ®, 200 mM EDTA) was added, mixed, and incubated for 15 minutes on ice. If lysis was not complete, it was further incubated for about 5 minutes at 37° C. The mixture was centrifuged at 20,000 rpm for 40 minutes. The supernatant was removed and retained. A CsCl gradient (density of 1.55) was made by adding 28.65 g of CsCl to 31.2 ml of DNA solution. The gradient solution was mixed to dissolve and transferred to large ultracentrifuge tubes. The tubes were filled with ~0.6 ml of ethidium bromide (10 mg/ml), sealed and mixed.

The gradient was centrifuged at 49,000 rpm for 18 hours. The lower band of plasmid DNA as visualized with long-wave UV light was collected. The ethidium bromide was removed by extracting 4 to 5 times with isoamyl alcohol. The DNA solution was dialyzed against 2 liters of TE buffer (10 mM Tris HCl, pH 8.0, 1 mM EDTA) and after 2 hours was replaced with fresh TE. The dialyzed solution was extracted twice with phenol and twice with chloroform:isoamyl alcohol (24:1). The DNA was ethanol precipitated by adding one-tenth volume of 3M sodium acetate and 3 volumes of ethanol. The DNA was collected by centrifugation for 10 minutes at 10,000 rpm, washed with 70% ethanol and then 100% ethanol, dried and dissolved in about 250 μl of sterile TE. The concentration and purity was estimated by measuring optical density at 260 and 280 nm. A restriction site and function map of the insert DNA of pKC644 is presented in FIG. 2 of the accompanying drawings.

EXAMPLE 2

Transformation of *Streptomyces ambofaciens* (NRRL 15263), *S. fradiae* GS14 (tylA mutant strain), *S. fradiae* GS50 (tylB mutant strain), and *S. fradiae* PM73 (tylB mutant strain)

A. List of Solutions
The following solutions are referred to throughout the Examples and are presented here for clarity.

| Ingredient | Amount |
|---|---|
| 1. P Medium (~100 ml): | |
| Sucrose | 10.3 g |
| $K_2SO_4$ | 0.025 g |
| Trace element solution (see #3) | 0.2 ml |
| $MgCl_2.6H_2O$ | 0.203 g |
| Water | 80 ml |
| After autoclaving add: | |
| $KH_2PO_4$ (0.5%) | 1 ml |
| $CaCl_2.2H_2O$ (3.68%) | 10 ml |
| (N-tris-(hydroxymethyl)-methyl-2-aminoethane sulphonic acid), "TES" buffer, 0.25M, pH = 7.2 | 10 ml |
| 2. Trace element solution (~1 L): | |
| $ZnCl_2$ | 40 mg |
| $FeCl_3.6H_2O$ | 200 mg |
| $CuCl_2.2H_2O$ | 10 mg |
| $MnCl_2.4H_2O$ | 10 mg |
| $Na_2B_4O_7.10H_2O$ | 10 mg |
| $(NH_4)_6Mo7O_{24}.4H_2O$ | 10 mg |
| $H_2O$ | 1 L |
| 3. R2 Regeneration Medium (~1 L): | |
| Sucrose | 103 g |
| $K_2SO_4$ | 0.25 g |
| Trace element solution | 2 ml |
| $MgCl_2.6H_2O$ | 10.12 g |
| glucose | 10 g |
| L-asparagine.$1H_2O$ | 2.0 g |
| casamino acids | 0.1 g |
| Agar | 22 g |
| Water | to 700 ml |
| The pH is adjusted to pH = 7.2 before autoclaving. After autoclaving, add: | |
| $KH_2PO_4$ (0.05 g/100 ml) | 100 ml |
| $CaCl_2$ (2.22 g/100 ml) | 100 ml |

-continued

A. List of Solutions
The following solutions are referred to throughout the Examples and are presented here for clarity.

| Ingredient | Amount |
|---|---|
| TES Buffer (5.73 g/100 ml, pH = 7.2) | 100 ml |
| 4. Soft Nutrient Agar (SNA, ~1 L): | |
| Difco Bacto Nutrient Broth | 8 g |
| Agar | 5 g |
| 5. R2YE medium is R2 medium with 20 ml of 25% yeast extract added per liter. | |
| 6. Yeast Extract - Malt Extract (YEME, ~1 L): | |
| Yeast extract | 3 g |
| Peptone | 5 g |
| Malt extract | 3 g |
| Glucose | 10 g |
| 7. YEME + 34% Sucrose Liquid Complete Media is YEME with 340 g/L of sucrose. | |
| 8. YMX Medium (~1 L): | |
| Yeast extract | 3 g |
| Malt extract | 3 g |
| Glucose | 2 g |
| 9. YMX Agar is 0.3% yeast extract, 0.3% malt extract, 0.2% dextrose, and 2.0% agar. | |
| 10. Tylosin Fermentation Medium | |
| Beet Molasses | 2% |
| Corn Meal | 1.5% |
| Fish Meal | 0.9% |
| Corn Gluten | 0.9% |
| Sodium Chloride | 0.1% |
| Ammonium Phosphate (dibasic) | 0.04% |
| Calcium Carbonate | 0.2% |
| Crude Soybean Oil | 3% |
| The pH of this medium was adjusted to 7.1 with 1N NaOH. | |
| 11. AS1 Medium (~1 L deionized $H_2O$) | |
| Yeast Extract | 1 g |
| L-alanine | 0.2 g |
| L-arginine (free base) | 0.2 g |
| L-asparagine | 0.5 g |
| Soluble Starch | 5 g |
| Sodium Chloride | 2.5 g |
| Sodium Sulfate | 10 g |
| Meer Agar | 20 g |
| 12. Spiramycin Fermentation Medium (~1 L) | |
| Yeast Extract | 10 g |
| KCl | 2.5 g |
| $MgSO_4$ | 0.1 g |
| $KH_2PO_4$ | 10 g |
| $FeCl_2$ | 0.03 g |
| $ZnCl_2$ | 0.03 g |
| $MnCl_2$ | 0.01 g |
| Ammonium Molybdate | 0.005 g |

These ingredients were dissolved in 800 ml of water and autoclaved. To this was added sterile potato dextrin (15 g) and glucose (10 g) in 200 ml of water.

B. Transformation of Streptomyces

Five ml of a fully grown overnight culture of Streptomyces, homogenized and sonicated, were used to inoculate 20 ml of TSB plus 0.3% glycine. The culture was incubated at 30° C. for 24 hours. After homogenization with a tissue grinder, 5 ml of homogenate was used to inoculate 20 ml of fresh TSB supplemented with 0.3% glycine. The culture was incubated at 30° C. for 24 hours. The culture was homogenized and transferred to a 50 ml sterile polystyrene centrifuge tube. The cells were pelleted by centrifugation for 10 minutes at 3500 rpm, washed with 10 ml of P medium and re-pelleted. The cells were then resuspended in 15–20 ml of P medium with 1 mg/ml lysozyme and incubated at room temperature for 1.5 hours. Protoplast formation was monitored by examining small samples under a phase-contrast microscope. Protoplasts are spherical.

The protoplasts were centrifuged as before and washed twice in P medium. The cells were resuspended in 20 ml of P medium and 200 μl of protoplasts for each transformation were placed in a 1.5 ml Eppendorf® tube. Up to 10 μl of DNA solution were added with gentle mixing. Nine hundred μl of 50% polyethylene glycol 1000 in P medium were added immediately. One half ml of transformation mix in 4 ml of modified R2 top agar was poured onto dried modified R2 plates. The plates were incubated at 30° C. for 24 hours. The plates were then overlaid with modified R2 top agar containing an appropriate amount of the desired antibiotic. With pHJL401-derived plasmids, thiostrepton was used at 50 μg/ml. With pOJ160 or pKC473 derived plasmids, apramycin was used at 50 μg/ml. When the Tn5 NmR gene was present, neomycin was used at 10 μg/ml. The plates were incubated at 30° C. and transformants appeared 2–3 days later (7–10 days with *S. fradiae*). The transformants were analyzed for the presence of appropriate plasmid DNA by the method of Example 3, set out below.

EXAMPLE 3

Rapid Isolation of Plasmid DNA from Streptomyces

The cells were grown in 25 ml of TSB supplemented with a suitable concentration of antibiotic. The cells were washed once in 10.3% sucrose, pelleted, and resuspended in 5 ml of lysozyme solution (5 mg/ml lysozyme in 0.3M sucrose, 25 mM Tris HCl, pH 8.0, 25 mM EDTA). The mixture was incubated for 30 minutes at room temperature and 2.5 ml of alkaline lysis solution (0.3M sodium hydroxide and 1% SDS) was added. Immediately, the solution was vortexed vigorously, then incubated at 50° C. for 30 minutes. The solution was then vortexed vigorously, then two ml of acid phenol:Sevag (chloroform:isoamyl alcohol, 24:1) were added, and the extraction was vortexed vigorously again. The layers were separated by centrifugation in a table mop centrifuge. The aqueous layer (~7 ml) was transferred into a tube containing 0.7 ml of 3M sodium acetate. An equal volume of 2-propanol was added and the mixture vortexed. Incubation was carried out for 10 minutes at room temperature. The DNA was pelleted by centrifugation for 10 minutes at 10,000 rpm. The liquid was decanted, centrifuged for 20 seconds, and the last traces of liquid removed with tissue paper.

The pellet was dissolved in 0.5 ml of TE buffer and transferred to an Eppendorf® tube containing 50 μl of 3M sodium acetate. The solution was extracted once with neutral phenol:Sevag, once with Sevag and then precipitated with an equal volume of 2-propanol. The mixture was centrifuged for 2 minutes and all of the liquid was removed as before. The pellet was redissolved in 0.5 ml of TE buffer and 5 μl of 0.5M spermine.HCl was added. The solution was mixed, incubated at room temperature for 5 minutes, and centrifuged for 5 minutes. The liquid was removed. The pellet was washed in 1 ml of a solution containing 70% ethanol, 0.3M sodium acetate and 10 mM magnesium acetate. The mixture was incubated for 5 minutes at room temperature and centrifuged for 5 minutes. The liquid was removed and the pellet dried. The pellet was redissolved in 25 μl of TE and 1–2 μl was used for each restriction enzyme digestion.

The aforementioned plasmid isolation procedures also useful for providing a source of DNA for hybridization studies utilizing the srmR probes of the present invention.

---

We claim:

1. An isolated DNA sequence encoding the SrmR activator protein of Streptomyces ambofaciens consisting of nucleotides 498–2312 of SEQ ID NO: 1:

ATG CGC CGA CTG GAG CGC TTC AAC

CGG CTC GCC CTC ACC GCG

CAG TCG ATG ATC GAG TAC CGC CGC

GAC CGG GAG GCG GAG CTC GCG

GCC CTG GTC GAC GCC GCG CAC GAG

TTC GTC GCC GCC CGG CGG GGC

AAG GAC CTG CTG GAG TCC ATC GCC

CGC AGA GCA CGG CTG CTG CTG

AAG CTG GAC GTC TCC TAC GTC GGC

CTG CAC GAG GAG GAC CGG CCC

GGC ACG GTG GTG CTG AGC GCC GAC

GGC AAC GCG GTC AAG GTC GCC

GAG AGC TAC CGG CTG CCG GCC GAC

GGC GGA CTG GGC GCC ATG GTG

CGC ACC TGC CGC GCT CCC TTC TGG

ACC CCG GAC TAC CTC GGG GAC

AAC AGC TTC ACG CAC GTC GAG GCC
GTC GAC GAC ATC GTC CGC GCC
GAA GGC CTG CGC GCG GTC CTG GCC
GTC CCG CTG TGC GCC GGG GGC
GAA CCG ATG GGG GTC CTC TAC GTC
GCC GAC CGT CAG GTG CGG CAT
CTG ACC CCC AAC GAG GTC ACC CTG
CTG TGC TCG CTC GCC GAT CTG
GCC GCG GTG GCG ATC GAG CGC AAC
CGG CTG GTC GAG GAG CTC CAC
GAC ACC ATC GGG CAA CTG CGC CAG
GAC ATC GGC GAG GCC CGC ACC
GCC CTC GCG CGC ACC CGC AGG TCC
GCC GAC CTC CAG TCG CAC CTG
GTC ACG CAG GTG ATG GAC AGG CGC
GGC GCC GAC TCG TTA CTC GCG
ACG GCC GCC GAG GCG CTC GGC GGC
GGA GCC GGC CTG TGC AGC CCG
CTC GGG CGC CCG CTC GCC GAG TAC
GGG ACC ATG CGC CCC GTC GCC
CCC ACG GAA CTG CGC GCG GCG TGC
CGC CGG GCC GCC GAG ACC GGC
CGG CCC ACC TCC GTG GCC CCG GGG
GTC TGG ACG GTG CCC CTG CTT
CCC GGG GGC AAC GCC GGC TTC CTG
CTG ACC GAC CTC GGT CCG GAC
GCG GAC CAC ACC GCC GTC CCC CTG
CTC CCG ATG GTC GCC CGC ACC
CTC GCG CTG CAC CTG CGC GTC CAG
CAC GAC GAC TCC CCC AAG GCG
CAG AGC CAC CAG GAG TTC TTC GAC
GAC CTG ATC GGG GCG CCC CGC
TCA CCC ACG CTC CTC AGG GAA CGC
GCC CTG ATG TTC TCC CTC AGC
TTC CGC CGC CCG CAC GTG GTG CTG
GTG GCG GGC GGA CCC CGC GGG
ACC TCG CCG CGG CTG GAC CGG TCC
GGC GCC GAC TAC GCG AAG GAG
CTC GGC GGG CTG TGC AGC GTG CGG
GAC GGC GCC GTC GTC CTG CTG
CTG CCC GGC GAC GAC CCC GTC GCC
GTG GCG CAG ACC GCC GCC CCG
GAG CTG ACC GAC CGC GCC GGG CAC

CCC GTC ACC GTG GGG GTC GCG

GGC CCC GCC TCG ACC GTC GAC GGC

ATC GCC GAC GCG CAC CGT GAG

GCC GCG AAG TGT CTG GAG ACC CTC

CGC GCG CTC GGC GGC GAC GGC

GGC ACC GCG TGC GCC TCC GAC CTG

GGT TTC CTC GGC ATG CTC CTC

GCC GAG GAG AAC GAC GTC CCC GGT

TAC ATC AGG ACG ACG ATC GGC

CCC GTG GTC GAC TAC GAC ACC CAC

CGC TTC ACG GAT CTG GTT CCC

ACT CTG AGG GTG TAC CTG GAG TCG

GGC AGG AGC CCC ACG CGT GCC

GCA GAG ACA CTG CGC GTG CAC CCG

AAC ACC GTC TCA CGG CGG CTG

GAG CGC ATC GGC GTA CTG CTG GGA

GAG GAC TGG CAG TCA CCG GAG

CGG GTG CTG GAC ATA CAA CTG GCC

CTG CGG CTC TAT CAG GTG CGC

TCG GCG CTC TCC TCG CAA CCG GCG

TCC GAG ACC CGG GCC GTG

CTC GGA TCG CTG CGC GAG TGA which is the coding region of Sequence ID1.

2. A method for identifying nucleic acids involved in macrolide biosynthetic pathways comprising:

(A) constructing probes corresponding to srmR coding sequence of Sequence ID1;

(B) contacting the probes of Step (A) with a DNA sample of interest; and

C) measuring the reactivity of the probes of step (A) with the DNA sample of interest of Step (B) to identify nucleic acids involved in macrolide biosynthetic pathways.

3. An isolated transcriptional activating sequence which is functional in *Streptomyces ambofaciens* and which has a DNA sequence consisting of nucleotides 1–344 of SEQ ID No:1:

```
TGCTCGTTCC GCCGGAAATC ACGGTGTGGC CCCCGGGCCA CCGGGTAGCT
TATGCCTCGT TCACCGCAGC GGTTGAAGAG GCAGCCTTCA ACCCCGGCCC
GGCCTTTATG GAATTCATTT CCACCGTGCC GCAACACCCC TGAAGGACGG
CCGGATATCG GCCATGAAGC CCCGGCCTTT CAGCCAGGCG CCCTCTCTTG
TCGAATAGAG TATGTCCTCC GCTGAAGCCG CCGAAGACGG ACGAAGGGGA
CGAACGGTCA CCTCGGTCGA TCTAGACGGA ATCCTTGAAA GCGTAATAGC
CTGTCAATGC TTTGGTAAAG CACAGGGATG GGGGTGCCTG CGGG
``` which is the 5' Region of Sequence ID1.

\* \* \* \* \*